United States Patent
Griswold-Prenner et al.

(10) Patent No.: US 10,766,954 B2
(45) Date of Patent: Sep. 8, 2020

(54) THERAPEUTIC ANTIBODIES FOR TREATMENT OF NEURODEGENERATION

(71) Applicant: Imago Pharmaceuticals, Inc., Jackson, WY (US)

(72) Inventors: Irene Griswold-Prenner, Jackson, WY (US); Karen Chen, New York, NY (US)

(73) Assignee: Imago Pharmaceuticals, Inc., Jackson, WY (US)

( * ) Notice: Subject to any disclaimer, the term of this patent is extended or adjusted under 35 U.S.C. 154(b) by 0 days.

(21) Appl. No.: 16/092,055

(22) PCT Filed: Apr. 5, 2017

(86) PCT No.: PCT/US2017/026062
§ 371 (c)(1),
(2) Date: Oct. 8, 2018

(87) PCT Pub. No.: WO2017/176835
PCT Pub. Date: Oct. 12, 2017

(65) Prior Publication Data
US 2019/0330315 A1   Oct. 31, 2019

Related U.S. Application Data

(60) Provisional application No. 62/319,229, filed on Apr. 6, 2016, provisional application No. 62/366,770, filed on Jul. 26, 2016.

(51) Int. Cl.
| | | |
|---|---|---|
| *C07K 16/18* | (2006.01) | |
| *A61P 25/00* | (2006.01) | |
| *A61P 25/28* | (2006.01) | |
| *A61P 25/16* | (2006.01) | |

(52) U.S. Cl.
CPC .............. *C07K 16/18* (2013.01); *A61P 25/00* (2018.01); *A61P 25/16* (2018.01); *A61P 25/28* (2018.01); *C07K 2317/56* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | | |
|---|---|---|---|---|
| 5,530,101 A | * | 6/1996 | Queen | C07K 16/00 424/133.1 |
| 2015/0196663 A1 | * | 7/2015 | Shusta | C07K 16/28 424/178.1 |
| 2015/0266947 A1 | * | 9/2015 | Sierks | G01N 33/6896 424/135.1 |
| 2017/0355756 A1 | * | 12/2017 | Julien | C07K 16/18 |

FOREIGN PATENT DOCUMENTS

| | | | |
|---|---|---|---|
| WO | WO 2008068048 | * | 12/2007 |
| WO | WO 2013049666 | * | 9/2012 |

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*

* cited by examiner

*Primary Examiner* — Adam Weidner
(74) *Attorney, Agent, or Firm* — Dianna L. DeVore

(57) ABSTRACT

The invention provides therapeutic antibodies and methods for treatment of diseases associated with diseases associated with aggregation of α-synuclein, e.g., in the brain of a subject. Such methods provide administration of therapeutic antibodies to elicit a beneficial immunogenic response against aggregation of α-synuclein. The methods are particularly useful for prophylactic and therapeutic treatment of diseases associated with the formation of Lewy bodies, e.g., Parkinson's disease.

12 Claims, 2 Drawing Sheets
Specification includes a Sequence Listing.

FIGURE 1

| Antibody (mIgG) | Dose (mg/kg) | CL (ml/day/kg) | $T_{1/2}$ (days) |
|---|---|---|---|
| IGP101 | 10 | 6.44 | 9.62 |
| 6H7 | 10 | 7.42 | 11.31 |
| 8A5 | 10 | 9.48 | 10.19 |
| 2A12 | 10 | 23.9 | 2.77 |
| Control Ab | 10 | 8.84 | 9.51 |

SEQUENCE LISTING

```
<160> NUMBER OF SEQ ID NOS: 11

<210> SEQ ID NO 1
<211> LENGTH: 11
<212> TYPE: PRT
<213> ORGANISM: Artificial Sequence
<220> FEATURE:
<223> OTHER INFORMATION: synthetic peptide

<400> SEQUENCE: 1

Lys Ser Leu Leu His Ser Asn Gly Asn Thr Tyr
1               5                   10

<210> SEQ ID NO 2
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 2
```

Arg Met Ser Xaa
1

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Met Gln His Leu Glu Phe Pro Phe Thr
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic peptide

<400> SEQUENCE: 4

Gly Phe Ser Phe Asn Thr Tyr Ala
1               5

<210> SEQ ID NO 5
<211> LENGTH: 10
<212> TYPE: PRT
<213> ORGANISM: Artificial Sequence
<220> FEATURE:
<223> OTHER INFORMATION: synthetic peptide

<400> SEQUENCE: 5

Thr Leu Ser Lys Ser Asn Asn Tyr Ala Thr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: synthetic peptide

<400> SEQUENCE: 6

Val Gly Ala Phe Ala Tyr
1               5

<210> SEQ ID NO 7
<211> LENGTH: 112
<212> TYPE: PRT
<213> ORGANISM: Artificial Sequence
<220> FEATURE:
<223> OTHER INFORMATION: synthetic peptide

<400> SEQUENCE: 7

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Phe Pro Phe Thr Phe Gly Ala Gly Thr Lys Leu Glu Leu Lys
            100                 105                 110

<210> SEQ ID NO 8
<211> LENGTH: 115
<212> TYPE: PRT
<213> ORGANISM: Artificial Sequence
<220> FEATURE:
<223> OTHER INFORMATION: synthetic peptide

<400> SEQUENCE: 8

Glu Val Gln Leu Val Glu Ser Gly Gly Gly Leu Val Gln Pro Lys Gly
1               5                   10                  15

Thr Leu Lys Leu Ser Cys Ala Ala Ser Gly Phe Ser Phe Asn Thr Tyr
            20                  25                  30

Ala Met Asn Trp Val Arg Gln Ala Pro Gly Lys Ser Leu Glu Trp Val
        35                  40                  45

Ala Arg Thr Leu Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Ser Leu Gln Met Asn Asn Leu Lys Thr Glu Asp Thr Ala Met Tyr
                85                  90                  95

Tyr Cys Val Gly Ala Phe Ala Tyr Trp Gly Gln Gly Thr Leu Val Thr
            100                 105                 110

Val Ser Ala
        115

<210> SEQ ID NO 9
<211> LENGTH: 140
<212> TYPE: PRT
<213> ORGANISM: Artificial Sequence
<220> FEATURE:
<223> OTHER INFORMATION: synthetic peptide

<400> SEQUENCE: 9

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

```
<210> SEQ ID NO 10
<211> LENGTH: 18
<212> TYPE: PRT
<213> ORGANISM: Artificial Sequence
<220> FEATURE:
<223> OTHER INFORMATION: synthetic peptide

<400> SEQUENCE: 10

Leu Gly Lys Asn Glu Glu Gly Ala Pro Gln Glu Gly Ile Leu Glu Asp
1               5                   10                  15

Met Pro

<210> SEQ ID NO 11
<211> LENGTH: 10
<212> TYPE: PRT
<213> ORGANISM: Artificial Sequence
<220> FEATURE:
<223> OTHER INFORMATION: synthetic peptide

<400> SEQUENCE: 11

Pro Gln Glu Gly Ile Leu Glu Asp Met Pro
1               5                   10
```

THERAPEUTIC ANTIBODIES FOR TREATMENT OF NEURODEGENERATION

CROSS REFERENCE TO RELATED APPLICATIONS

This application claims priority to U.S. Provisional Application 62/319,229, filed Apr. 6, 2016, and U.S. Provisional Application 62/366,770, filed Jul. 26, 2016, which are hereby incorporated by reference in their entirety for all purposes.

FIELD OF THE INVENTION

This invention relates to therapeutic antibodies and methods for the treatment of neurodegenerative disease.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Accumulation of the α-synuclein protein has been associated with several neurodegenerative diseases, termed synucleinopathies. These diseases share the same feature, insoluble inclusions in the neurons and the glia of the brain called Lewy bodies which are composed primarily of α-synuclein. Lewy bodies and Lewy neurites are the neuropathological hallmarks Parkinson's disease (PD) and other diseases including diffuse Lewy body disease (DLBD), Lewy body variant of Alzheimer's disease (LBVAD), combined PD and Alzheimer's disease (AD), multiple systems atrophy (MSA) and Dementia with Lewy bodies (DLB).

AD, PD, MSA and DLB are the most common neurodegenerative disorders in the elderly. Although each neurodegenerative disease appears to have a predilection for specific brain regions and cell populations, resulting in distinct pathological features, PD, AD, MSA, DLB and LBD also share common pathological hallmarks. Subjects with familial AD, Down syndrome, or sporadic AD develop LBs on the amygdala, which are the classical neuropathological hallmarks of PD. Additionally, each disease is associated with the degeneration of neurons, interneuronal synaptic connections and eventually cell death, the depletion of neurotransmitters, and abnormal accumulation of misfolded proteins, the precursors of which participate in normal central nervous system function. Biochemical studies have confirmed the link between AD, PD, MSA and DLB.

The present invention is directed to treatment of PD and other synucleinopathies associated with Lewy bodies by administration of therapeutic antibodies that selectively bind to an epitope of α-synuclein to a subject under conditions that generate a beneficial response in the subject. The invention addresses a significant clinically unmet need for therapeutic regimes for preventing or ameliorating the neuropathology and cognitive impairment associated with PD and other diseases associated with Lewy bodies.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides therapeutic antibodies and active fragments thereof for the treatment of neurodegenerative diseases, and in particular in the treatment of synucleinopathies. The therapeutic antibodies of the invention are preferably monoclonal antibodies that specifically bind to an epitope on a peptide (SEQ ID NO:10) which corresponds to amino acids 100-117 of full-length human α-synuclein (SEQ ID NO:9).

In one embodiment, the invention provides a therapeutic monoclonal antibody comprising sequences with substantial identity to the $V_L$ CDRs of SEQ ID NO:1, SEQ NO:2 and/or SEQ NO: 3. In a specific embodiment, the invention provides a therapeutic monoclonal antibody comprising a $V_L$ region with substantial identity to SEQ NO:7.

In another embodiment, the invention provides a therapeutic monoclonal antibody comprising sequences with substantial identity to the $V_H$ CDRs of SEQ ID NO:4, SEQ NO:5 and/or SEQ NO:6. In a specific embodiment, the invention provides a therapeutic monoclonal antibody comprising a $V_H$ region with substantial identity to SEQ NO:8.

In a preferred embodiment, the invention provides a therapeutic antibody comprising a $V_L$ region with substantial identity to SEQ NO:7 and a $V_H$ region with substantial identity to SEQ NO:8.

The therapeutic antibody used in human subjects can be human, humanized, chimeric, or bispecific. In some methods the isotype of the antibody is a human IgG1. The humanized antibody may comprise a heavy chain region of the isotype IgG1, IgG2, IgG3, or IgG4.

In certain aspects, the therapeutic antibody of the invention is a humanized monoclonal antibody. In specific aspects, the therapeutic antibody of the invention is a humanized form of the monoclonal antibody deposited at American Type Culture Collection under accession number PTA-9197.

In some specific embodiments, the therapeutic antibody of the invention is an Fv, scFv, Fab, F(ab')2, or Fab'.

This invention further provides pharmaceutical compositions comprising any of the therapeutic antibodies or active fragments thereof, as described in this application, and a pharmaceutically acceptable carrier.

In another aspect, the invention provides methods of preventing or treating a disease characterized by Lewy bodies or α-synuclein aggregation comprising administering a therapeutic antibody or active fragment thereof to a subject in need of such treatment.

The invention also provides methods of preventing or treating a disease characterized α-synuclein aggregation (e.g., Lewy bodies) in the brain. Such methods entail administration of a therapeutic antibody of the invention or an active fragment thereof that specifically binds to α-synuclein, as described in more detail herein. In some methods, the subject has the disease and may be symptomatic or asymptomatic. In other methods the subject has a risk factor for the disease and is asymptomatic. In some methods, the α-synuclein aggregation disease is PD. In yet other methods, the α-synuclein aggregation disease is DLB. In still other methods, the α-synuclein aggregation disease is PD associated with AD. In other methods, the α-synuclein aggregation disease is MSA.

The present invention provides methods of treatment of neurodegeneration using a therapeutic antibody that comprises $V_L$ CDRs with substantial identity to SEQ ID NO:1, SEQ ID NO:2 or SEQ ID NO:3. In other embodiments, the invention provides methods using a therapeutic antibody that comprises $V_L$ CDRs with substantial identity to SEQ ID NO:1 and SEQ ID NO:2. In other embodiments, the invention provides methods using a therapeutic antibody that comprises $V_L$ CDRs with substantial identity to SEQ ID NO:2 and SEQ ID NO:3. In still other embodiments, the invention provides methods using a therapeutic antibody that comprises $V_L$ CDRs with substantial identity to SEQ ID NO:1 and SEQ ID NO:3. In a specific embodiment, the invention provides methods using a therapeutic antibody that comprises $V_L$ CDRs with substantial identity to SEQ ID NO:1, SEQ ID NO:2 and SEQ ID NO:3.

The present invention also provides methods of treatment of neurodegeneration using a therapeutic antibody that comprises $V_H$ CDRs with substantial identity to SEQ ID NO:4, SEQ ID NO:5 or SEQ ID NO:6. In other embodiments, the invention provides methods using a therapeutic antibody that comprises $V_H$ CDRs with substantial identity to SEQ ID NO:4 and SEQ ID NO:5. In other embodiments, the invention provides methods using a therapeutic antibody that comprises $V_H$ CDRs with substantial identity to SEQ ID NO:5 and SEQ ID NO:6. In still other embodiments, the invention provides methods using a therapeutic antibody that comprises $V_H$ CDRs with substantial identity to SEQ ID NO:4 and SEQ ID NO:6. In a specific embodiment, the invention provides methods using a therapeutic antibody that comprises $V_H$ CDRs with substantial identity to SEQ ID NO:4, SEQ ID NO:5 and SEQ ID NO:6.

In some embodiments, the present invention provides methods of treatment of neurodegeneration using a therapeutic antibody that comprises a $V_L$ region with substantial identity to SEQ NO:7. In other methods, the antibody administered to the subject in need of treatment is a monoclonal antibody with substantial identity to the $V_H$ region with substantial identity to SEQ NO:8. In a specific embodiment, the invention provides a method of treating a disease characterized by α-synuclein aggregation, comprising administering to a subject having or at risk of the disease a therapeutic antibody comprising a $V_L$ region with substantial identity to SEQ NO:7 and a $V_H$ region with substantial identity to SEQ NO:8.

In yet another specific embodiment, the invention provides a method of treating a disease characterized by α-synuclein aggregation in the brain, comprising administering to a subject having or at risk of the disease a therapeutic antibody that specifically binds to a peptide of SEQ ID NO:9.

The present invention also provides a therapeutic antibody that comprises a $V_L$ CDR with a binding region that is at least 80% conserved, more preferably 90% conserved, with SEQ ID NO:1. In other method of the invention, the invention provides a therapeutic antibody that comprises a $V_L$ CDR with a binding region that is at least 66% conserved with SEQ ID NO:2. In still other methods of the invention, the invention provides a therapeutic antibody that comprises a $V_L$ CDR with a binding region that is at least 77% conserved, more preferably at least 88% conserved with SEQ ID NO:3. In a preferred embodiment, the invention provides a therapeutic antibody that comprises $V_L$ CDRs that are substantially conserved with the binding regions of CDRs of SEQ ID NO:1, SEQ NO:2 and SEQ NO: 3. In a specific embodiment, the invention provides a therapeutic antibody that comprises a $V_L$ region that is at least 80% conserved, more preferably at least 90% conserved, even more preferably 95% conserved with SEQ ID NO:7.

The present invention also provides a therapeutic antibody that comprises a $V_H$ CDR with a binding region that is at least 77% conserved, with SEQ ID NO:4. In other method of the invention, the invention provides a therapeutic antibody that comprises a $V_H$ CDR with a binding region that is at least 80% conserved, more preferably 90% conserved with SEQ ID NO:5. In still other methods of the invention, the invention provides a therapeutic antibody that comprises a $V_H$ CDR with a binding region that is at least 83% conserved with SEQ ID NO:6. In a preferred embodiment, the invention provides a therapeutic antibody that comprises $V_H$ CDRs that substantially conserved with the binding regions of CDRs of SEQ ID NO:4, SEQ NO:5 and SEQ NO: 6. In a specific embodiment, the invention provides a therapeutic antibody that comprises a $V_H$ region that is at least 80% conserved, more preferably at least 90% conserved, even more preferably 95% conserved with SEQ ID NO:8.

The present invention also provides an active fragment of a therapeutic antibody that comprises a $V_L$ CDR with a binding region that is at least 80% conserved, more preferably 90% conserved, with SEQ ID NO:1. Other methods of the invention provide administration of an active fragment of a therapeutic antibody that comprises a $V_L$ CDR with a binding region that is at least 66% conserved with SEQ ID NO:2. In still other methods, the invention provides administration of an active fragment of a therapeutic antibody that comprises a $V_L$ CDR with a binding region that is at least 77% conserved, more preferably at least 88% conserved with SEQ ID NO:3. In a preferred embodiment, the invention provides administration of an active fragment of a therapeutic antibody that comprises $V_L$ CDRs that are substantially conserved with the binding regions of CDRs of SEQ ID NO:1, SEQ NO:2 and SEQ NO: 3. In a specific embodiment, the invention provides administration of an active fragment of a therapeutic antibody that comprises a $V_L$ region that is at least 80% conserved, more preferably at least 90% conserved, even more preferably 95% conserved with SEQ ID NO:7.

The present invention also provides an active fragment of a therapeutic antibody that comprises a $V_H$ CDR with a binding region that is at least 77% conserved, with SEQ ID NO:4. The invention also provides administration of an active fragment of a therapeutic antibody that comprises a $V_H$ CDR with a binding region that is at least 80% conserved, more preferably 90% conserved with SEQ ID NO:5. In still other methods the invention provides administration of an active fragment of a therapeutic antibody that comprises a $V_H$ CDR with a binding region that is at least 83% conserved with SEQ ID NO:6. In a preferred embodiment, the invention provides administration of an active fragment of a therapeutic antibody that comprises $V_H$ CDRs that substantially conserved with the binding regions of CDRs of SEQ ID NO:4, SEQ NO:5 and SEQ NO: 6. In a specific embodiment, the invention provides administration of an active fragment of a therapeutic antibody that comprises a $V_H$ region that is at least 80% conserved, more preferably at least 90% conserved, even more preferably 95% conserved with SEQ ID NO:8.

In specific methods, the invention provides a method of treating a neurodegenerative disease by administering a therapeutic antibody that competes for binding with an antibody that selectively binds to the peptide of SEQ ID NO:9.

In some methods the therapeutic antibody of the invention is administered in multiple doses over a period of at least six months. In some methods, the therapeutic antibody of the invention is administered with an adjuvant that enhances the immune response to α-synuclein in the treated subject.

In some methods, the antibody is administered with a pharmaceutical carrier. In some methods, the antibody or the active fragment thereof is administered at a dosage of 0.0001 to 100 mg/kg, preferably, at least 1 mg/kg body weight antibody. In some methods the antibody is administered in multiple doses over a prolonged period, for example, at least six months. In some methods antibodies can be administered as a sustained release composition. In some methods, the subject is monitored for level of administered antibody in the blood of the subject.

These aspects and other features and advantages of the invention are described below in more detail. Those skilled in the art will recognize, or be able to ascertain using no more than routine experimentation, many equivalents to the specific embodiments of the invention described herein. Such equivalents are intended to be encompassed by the claims.

BRIEF DESCRIPTION OF THE FIGURES

FIG. 1 is a table showing the various doses and in vivo half-life of the anti-α-synuclein antibodies administered to mice.

DEFINITIONS

Figure 2:
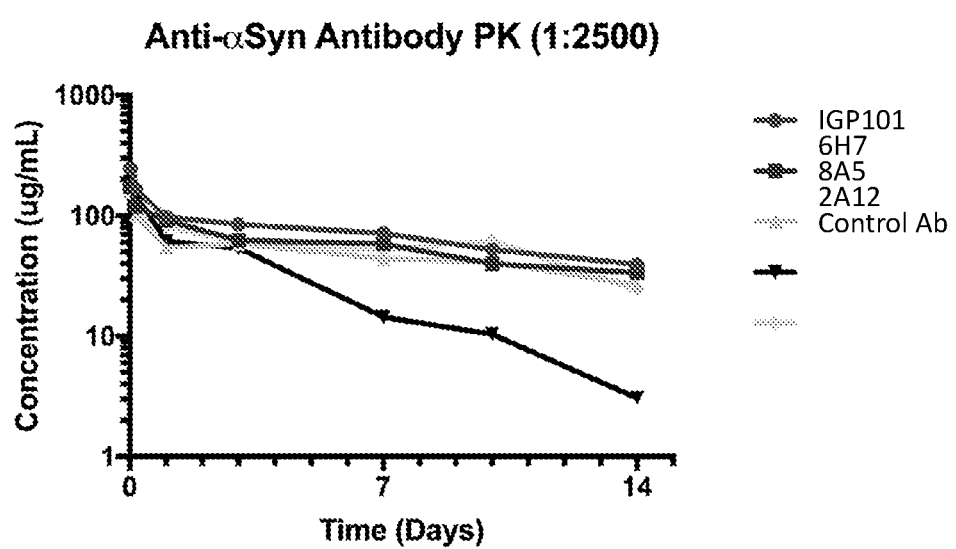
FIG. 2 is a line graph showing the in vivo half-life of the tested anti-α-synuclein antibodies in a single dose pharmacokinetic study.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "substantial identity" means that two peptide sequences, when optimally aligned, such as by the programs GAP or BESTFIT using default gap weights, share at least 66 to 90 percent sequence identity, preferably at least 77 to 95 percent sequence identity. Preferably, residue positions which are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (NCBI) website. Typically, default program parameters can be used to perform the sequence comparison, although customized parameters can also be used. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89, 10915 (1989)).

For purposes of classifying amino acids substitutions as conservative or non-conservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Therapeutic antibodies of the invention are typically substantially pure from undesired contaminant. This means that an antibody is typically at least about 50% w/w (weight/weight) purity, as well as being substantially free from interfering proteins and contaminants. Sometimes the therapeutic antibodies are at least about 80% w/w and, more preferably at least 90 or about 95% or higher w/w purity.

The phrase "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of a therapeutic antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1998) Using Antibodies, A Laboratory Manual, Cold Spring Harbor Laboratory press, New York, for a description of immunoassay formats and conditions that can be used to determine specific immunoreactivity. Specific binding between two entities means an affinity of at least $10^6$, $10^7$, $10^8$, $10^9$ or $10^{10}$ M$^{-1}$. Affinities greater than $10^8$ M$^{-1}$ are preferred.

The term "antibody" is used to include full-length antibodies and active fragments thereof that specifically bind to an epitope on an antigen. Active fragments include, but are not limited to, heavy chains, light chains, Fab, Fab' F(ab')$_2$, Fabc, and Fv. Fragments can be produced by, e.g., recombinant molecular techniques, enzymatic cleavage or chemical separation of intact antibodies. The term "antibody" as used herein is also intended to include one or more immunoglobulin chains fused (e.g., chemically conjugated to or connected through recombinant means) with other proteins. The term "antibody" as used herein also includes bispecific antibodies which include two different heavy/light chain pairs and two different binding sites (see, e.g., Songsivilai &

Lachmann, Clin. Exp. Immunol. 79:315-321 (1990); Kostelny et al., J. Immunol. 148, 1547-1553 (1992).

An "antigen" is any molecule (e.g., protein or peptide) to which a therapeutic antibody specifically binds.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

A "therapeutically effective amount" refers to the amount of an anti-synuclein antibody that, when administered to a mammal or other subject for treating a disease, is sufficient to effect such treatment for the disease. The "therapeutically effective amount" will vary depending on the anti-synuclein antibody, the disease and its severity and the age, weight, etc., of the subject to be treated.

As used herein, the term "affinity" refers to the equilibrium constant for the reversible binding of two agents (e.g., an antibody and an antigen) and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "selectively binds" are used interchangeably herein with respect to antibodies and/or antigen-binding fragments.

A "complementarity determining region" ("CDR") as described herein refers to a part of the variable chains in a therapeutic antibody where the molecule binds to the specific antigen. The CDRs of the antibodies of the invention are defined, e.g., using the method described in Lefranc M-P et al., Developmental and Comparative Immunology 27 (2003) 55-77.

The term "epitope" refers to a site on an antigen. An epitope typically includes at least 3-10, and more usually, at least 5-10 or more amino acids in a unique spatial conformation, which may be contiguous or non-contiguous based on the amino acids which form the epitope upon tertiary folding of a protein.

The term "immunological" or "immune" response is the development of a beneficial humoral (antibody mediated) and/or a cellular (mediated by antigen-specific T cells or their secretion products) response directed against an amyloid peptide in a recipient subject. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays ($CD4^+$ T cells) or CTL (cytotoxic T lymphocyte) assays (see Burke et al., *J Virol.* 2007 July; 81(14):7424-34; Tigges M A et al., *J Virol.* 1992 March; 66(3):1622-34). The relative contributions of humoral and cellular responses to the protective or therapeutic effect of an immunogen can be distinguished by separately isolating antibodies and T-cells from an immunized syngeneic animal and measuring protective or therapeutic effect in a second subject.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The phrase "competes for binding with" when used in reference to a therapeutic antibody refers to the ability of two or more antibodies to compete for binding to the same epitope. Competition between antibodies is determined by an assay in which the immunoglobulin under test inhibits specific binding of a reference antibody to a common antigen, such as α-synuclein. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, Using Antibodies, A Laboratory Manual, Cold Spring Harbor Laboratory Press (1988)); solid phase direct label RIA using I-125 label (see Morel et al., Molec. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%.

DETAILED DESCRIPTION OF THE INVENTION

The practice of the techniques described herein may employ, unless otherwise indicated, conventional techniques and descriptions of cell biology, cell culture, molecular biology (including recombinant techniques), biochemistry, therapeutic formulations, stem cell differentiation, all of which are within the skill of those who practice in the art. Such conventional techniques include recombinant molecular techniques complementary or useful to the methods described herein and technologies for formulating and/or administering biologic therapeutics. Specific illustrations of suitable techniques can be had by reference to the examples herein.

Such conventional techniques and descriptions can be found in standard laboratory manuals such as See, for example, Molecular Cloning A Laboratory Manual, 4th Ed., ed. by Green and Sambrook, (Cold Spring Harbor Laboratory Press: 2012); Molecular Biology of the Cell, ed. By B. Alberts (Garland Science, 2014); Oligonucleotide Synthesis: Methods and Applications (Methods in Molecular Biology), ed. by P. Herdewijn (Humana Press 2004); Mullis et al. U.S. Pat. No. 4,683,195; Nucleic Acids Hybridization: Modern Applications, ed. by Buzdin and Lukyanov (Springer, 2010); Antibodies: Volume 1: Production and Purification (G. Subramanian, 2004); Protein Chromatography: Methods and Protocols (Methods in Molecular Biology) ed. by D. Walls and S. T. Loughran, 2010); Gene Transfer and Expression in Mammalian Cells (New Comprehensive Biochemistry) ed. by S. C. Makrides (Eselvier, 2003); Immunochemical Protocols (Methods in Molecular Biology, ed. R. Burns (Humana Press, 2004); Therapeutic Antibodies (Handbook of Experimental Pharmacology), ed. Y. Chernajovsky and A. Nissim (Springer 2007); Manipulating the Mouse Embryo: a Laboratory Manual, $4^{th}$ edition, ed. by R. Behringer and M Gertsenstein (Cold Spring Harbor Laboratory Press, Cold Spring Harbor, N.Y., 2013), all of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells with various pluripotency and expression patterns, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

THE INVENTION IN GENERAL

The present invention provides methods of treating neurodegenerative diseases and conditions characterized by presence of deposits of α-synuclein peptide aggregated to an insoluble mass in the brain of a subject, e.g., in the form of Lewy bodies as well as therapeutic monoclonal antibodies for use in such methods. Without being bound by or limited to a mechanism, it is proposed that the therapeutic monoclonal antibodies of the invention can generate an immunogenic response to α-synuclein which acts to clear and/or prevent formation of α-synuclein deposits within cells, e.g., cells in the brain. Although an understanding of mechanism is not essential for practice of the invention, the immunogenic response can induce clearing as a result of antibodies to synuclein that are internalized within cells alone or with α-synuclein. Alternatively or additionally, antibodies can interfere with aggregation of α-synuclein on the cell exterior surface. For example, antibodies to α-synuclein may recognize and crosslink abnormally conformed proteins in the neuronal cells surface.

IGP101 is a monoclonal antibody that has been shown herein to specifically bind to an epitope on a peptide (SEQ ID NO:10) which corresponds to amino acids 100-117 of full-length human α-synuclein (SEQ ID NO:9). The CDRs of the $V_L$ and $V_H$ of IGP101 have been characterized, and correspond to SEQ ID NOs: 1-6 as described in more detail herein.

The binding ability of IGP101 as provided primarily by the characterized CDRs is used herein as the basis for the development of therapeutic monoclonal antibodies for the treatment of disease associated with α-synuclein aggregation in human subjects, e.g., disease associated with α-synuclein aggregation in the brain of human subjects. Such antibodies can be optimized using a variety of exemplary techniques as described in greater detail herein. The invention is intended to include therapeutic antibodies made by these techniques and other equivalents and improvements as may be used or developed.

Administration of a therapeutically effective amount of a therapeutic antibody comprising CDRs of the IGP101 antibody (or optimized CDRs developed therefrom) will decrease α-synuclein aggregation in the brain of mouse models of human α-synuclein aggregation. Thus, in one aspect, the invention provides a method for treatment of a disease characterized by α-synuclein aggregation in the brain comprising administration of one or more antibodies that specifically bind to an epitope on amino acids 100-117 of human α-synuclein. Compositions of the invention for treatment of a disease characterized by Lewy bodies or α-synuclein aggregation include dosage forms and formulations containing one or more such antibodies that specifically bind to the epitope of amino acids 100-117 of human α-synuclein. Exemplary formulations are known in the art and include those described below in the section entitled "Administration of α-synuclein Therapeutic Antibodies."

Humanized Therapeutic Monoclonal Antibodies

The IGP101 antibody can be used to form humanized and/or chimeric antibodies that specifically bind to bind to an epitope on amino acids 100-117 of human α-synuclein. Such humanized therapeutic monoclonal antibodies are preferred therapeutic antibodies of the invention.

Humanized antibodies have variable region framework residues substantially from a human therapeutic antibody (termed an acceptor antibody) and complementarity determining regions substantially from a mouse-antibody, (referred to as the donor immunoglobulin). See, Queen et al., Proc. Natl. Acad. Sci. USA 86:10029-10033 (1989), WO 90/07861, U.S. Pat. Nos. 5,693,762, 5,693,761, 5,585,089, 5,530,101, and Winter, U.S. Pat. No. 5,225,539. The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human therapeutic antibody sequences. The human therapeutic antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid: i) noncovalently binds antigen directly, ii) is adjacent to a CDR region, iii) otherwise interacts with a CDR region (e.g. is within about 6 A of a CDR region), or iv) participates in the $V_L$-$V_H$ interface.

Other candidates for substitution are acceptor human framework amino acids that are unusual for a human antibody at that position. These amino acids can be substituted with amino acids from the equivalent position of the mouse donor antibody or from the equivalent positions of more typical human antibodies. Other candidates for substitution are acceptor human framework amino acids that are unusual for a human antibody at that position. The preferred variable region frameworks of humanized antibodies usually show at least 75%, more preferably 80%, and even more preferably 85% sequence identity to a human variable region framework sequence or consensus of such sequences.

The humanized antibodies of the present invention preferably comprise CDR sequences derived from or based on mouse monoclonal antibody IGP101. The cell line designated producing the antibody IGP101 has the ATCC accession number PTA-9197, and was deposited under the provisions of the Budapest Treaty with the American Type Culture Collection (ATCC, Manassas, Va. 20108) on May 8, 2008.

A number of methods are known for producing chimeric and humanized antibodies using a therapeutic antibody-expressing a hybridoma. For example, the cloned immunoglobulin variable regions of the mouse IGP101 antibody can be used as the basis for producing such antibodies. In one method, for illustration and not limitation, the heavy chain variable $V_H$ region is cloned by RT-PCR using mRNA prepared from hybridoma cells. Consensus primers are employed to $V_H$ region leader peptide encompassing the translation initiation codon as the 5' primer and a g2b constant regions specific 3' primer. Exemplary primers are described in U.S. patent publication US2005/000915. The sequences from multiple, independently-derived clones, can be compared to ensure no changes are introduced during amplification. The sequence of the $V_H$ region can also be determined or confirmed by sequencing a $V_H$ fragment obtained by 5' RACE RT-PCR methodology and the 3' g2b specific primer.

The light chain variable $V_L$ region of IGP101 can be cloned in an analogous manner as the $V_H$ region. In one approach, a consensus primer set designed for amplification of murine $V_L$ regions is designed to hybridize to the $V_L$ region encompassing the translation initiation codon, and a 3' primer specific for the murine Ck region downstream of the V-J joining region. In a second approach, 5'RACE RT-PCR methodology is employed to clone a $V_L$ encoding cDNA. Exemplary primers are described in US2005/000915. The cloned sequences are then combined with sequences encoding human constant regions.

In one approach, the heavy and light chain variable regions are re-engineered to encode splice donor sequences downstream of the respective VDJ or VJ junctions, and cloned into the mammalian expression vector, such as pCMV-hγ1 for the heavy chain, and pCMV-hκ1 for the light chain. These vectors encode human γ1 and Ck constant regions as exonic fragments downstream of the inserted variable region cassette. Following sequence verification, the heavy chain and light chain expression vectors can be co-transfected into COS cells to produce chimeric antibodies. Conditioned media is collected 48 hours post transfection and assayed by western blot analysis for antibody production or ELISA for antigen binding. The chimeric antibodies are preferably humanized as described above.

The heavy and light chain variable regions of chimeric and/or humanized antibodies can be linked to at least a portion of a human constant region of choice. The choice of constant region may be driven by the desired mechanism of action of the antibody, e.g., whether cellular mediated toxicity is desired. For example, isotopes IgG1 and IgG3 have antibody-dependent complement activity and isotypes IgG2 and IgG4 do not. Choice of isotype can also affect passage of antibody into the brain. Human isotype IgG1 is preferred. Light chain constant regions can be lambda or kappa. Antibodies can be expressed as tetramers containing two light and two heavy chains, as separate heavy chains, light chains, as Fab, Fab' F(ab')2, and Fv, or as single chain antibodies in which heavy and light chain variable domains are linked through a linker.

Human Therapeutic Monoclonal Antibodies

The IGP101 antibody can be used to form humanized and/or chimeric antibodies that specifically bind to bind to an epitope on amino acids 100-117 of full-length human α-synuclein. Such humanized therapeutic monoclonal antibodies are preferred therapeutic antibodies of the invention.

Human antibodies against α-synuclein are provided by a variety of techniques described below. Some human antibodies can be selected by competitive binding experiments to have the same epitope specificity as IGP101. Human antibodies can also be screened for epitope specificity by using only the peptide of α-synuclein corresponding to amino acids 100-117 of full-length human α-synuclein as the immunogen, and/or by screening antibodies against a collection of deletion mutants of α-synuclein. Human antibodies of the invention can comprise a heavy chain region of the isotype IgG1, IgG2, IgG3, or IgG4, but in a preferred embodiment the antibodies of the invention have the isotype specificity of human IgG1. As described above, the human constant region may be selected based on the desired mechanism of action of the antibody.

One particular method for selecting such human antibodies is the use of phage display technology. This methodology may use antibody screening techniques as described, e.g., in Dower et al., WO 91/17271 and McCafferty et al., WO 92/01047, U.S. Pat. Nos. 5,877,218, 5,871,907, 5,858,657, 5,837,242, 5,733,743 and 5,565,332. In these methods, libraries of phage are produced in which different antibodies are provided on the outer surfaces of the phage. The antibodies are usually displayed on the phage as $F_v$ or $F_{ab}$ fragments. Antibodies with a desired specificity for the epitope are selected by affinity to an epitope of α-synuclein corresponding to the epitope of amino acids 100-117 of full-length human α-synuclein.

In a particular exemplary method, human antibodies that selectively bind to an epitope of α-synuclein corresponding to the epitope of amino acids 100-117 of full-length human α-synuclein can be produced using the technique of Winter, WO 92/20791. In this method, either the heavy or light chain variable region of IGP101 is used. If a light chain variable region is selected as the starting material, a phage library is constructed in which members display the light chain variable region of IGP101 and a different heavy chain variable region. The heavy chain variable regions are obtained from a library of rearranged human heavy chain variable regions. A phage showing strong specific binding for an epitope of α-synuclein corresponding to the epitope of amino acids 100-117 of full-length human α-synuclein is selected. The human heavy chain variable region from this phage provides the basis for constructing an optimized phage library in which each phage displays the same heavy chain variable region identified from the first display library and a different light chain variable region. The light chain variable regions are obtained from a library of rearranged human variable light chain regions. Phage that display the variable regions of completely human anti-α-synuclein antibodies and show strong specific binding for the epitope of amino acids 100-117 of full-length human α-synuclein is selected. These antibodies will be selected to have the same or similar epitope specificity as IGP101.

Transgenic Non-Human Mammals

Human antibodies against α-synuclein can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., US Pat App Nos. 20140041067, 20130347138, 20130263292, 20130243759, 20130219535, 20130042331, 20120204278, 20120167237, WO93/1222, U.S. Pat. Nos. 9,253,965, 9,206,263, 9,206,262, 9,206,261, 9,204,624, 9,193,977, 5,877,397, 5,874,299, 5,814,318, 5,789,650, 5,770,429, 5,661,016, 5,633,425, 5,625,126, 5,569,825, 5,545,806, Lonberg et al., Nature 148, 1547-1553 (1994), Lonberg et al., Nature Biotechnology 14, 826 (1996). Transgenic mice are particularly suitable. Anti-α-synuclein antibodies are obtained by immunizing a transgenic nonhuman mammal, such as the cited patents and publications, with a peptide containing the epitope of α-synuclein corresponding to the epitope of amino acids 100-117 of full-length human α-synuclein. Immunization may, for example, use the peptide corresponding amino acids 100-117 of full-length human α-synuclein, a larger peptide containing the epitope of α-synuclein corresponding to the epitope of amino acids 100-117 of full-length human α-synuclein, or a conjugate molecule comprising either of the two.

Conjugate molecules for use in immunization of the transgenic mice include peptides in combination with suitable carriers including but not limited to serum albumins, immunoglobulin molecules, thyroglobulin, ovalbumin, a T cell epitope, an immunostimulatory polymer, a toxoid from a pathogenic bacteria, such as tetanus, diphtheria, *E. coli*, cholera, or *H. pylori*, or an attenuated toxin derivative.

Recombinant Expression of Therapeutic Antibodies

Chimeric, humanized and/or human antibodies of the invention can be produced by recombinant expression. Recombinant nucleic acid constructs typically include an expression promoter operably linked to the nucleic acids encoding the antibody chains. The expression promoter can be the naturally occurring promoter of an exogenous promoter. Preferably, the expression control sequences are eukaryotic promoter systems in vectors capable of transforming or transfecting eukaryotic host cells. Once the vector has been incorporated into the appropriate host cell, the host cell is maintained under conditions suitable for high level expression of the nucleotide sequences, and the collection and purification of the recombinantly produced antibodies. Preferably, expression vectors contain selection sequences, e.g., ampicillin-resistance or hygromycin-resistance, to permit isolation of those cells successfully transformed with the recombinant antibody nucleic acids.

Although prokaryotic hosts such as *E. coli* or *Saccharomyces* may be used, mammalian cells are preferred host cells for expression of the recombinant antibodies. See, e.g., Li F et al., MAbs. 2010 September-October; 2(5): 466-477; Rita C A Eur J Pharm Biopharm. 2010 February; 74(2):127-38. A number of suitable host cell lines capable of successfully producing recombinant monoclonal antibodies are available, including but not limited to CHO cell lines, various COS cell lines, HeLa cells, L cells, human embryonic kidney cell, and myeloma cell lines. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are described in Gene Transfer and Expression in Mammalian Cells (New Comprehensive Biochemistry) ed. by S. C. Makrides (Eselvier, 2003).

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Green and Sambrook et al., supra).

Once expressed, antibodies can be purified according to standard procedures of the art, including HPLC purification, column chromatography, gel electrophoresis and the like (see generally, Protein Purification: Principles, High Resolution Methods, and Applications, by J-C Janson (Wiley, 2011).

Once a human or humanized monoclonal antibody is produced, the therapeutic antibodies of the invention can be tested for the ability to reduce α-synuclein aggregation and/or symptoms associated with α-synuclein aggregation. Such screening methods include in vitro methods, ex vivo methods, (e.g. methods utilizing tissue samples from the brain of a human subject with PD or a Lewy body disorder), or in vivo methods such as methods using animal models with symptoms characteristic of a synucleinopathy. Exemplary methods for screening antibodies for activity against α-synuclein are taught, for example, in U.S. Pat. No. 7,919,088.

Treatment of Subjects with Synucleinopathies

Exemplary subjects amenable to treatment with the therapeutic antibodies and methods of the invention include individuals diagnosed and/or presently showing symptoms of a synucleinopathic disease as well as subjects at risk of a synucleinopathic disease but not yet symptomatic. Subjects amenable to treatment include individuals at risk of or diagnosed with a disease associated with α-synuclein aggregation, e.g. PD, DLB, DLBD, LBVAD, combined PD and AD, Lewy body dysphagia, an inherited Lewy body disease (e.g., mutations of the α-synuclein gene, PARK3 and PARK4) and multiple system atrophy (e.g., olivopontocerebellar atrophy, striatonigral degeneration and Shy-Drager syndrome).

In certain aspects, the invention provides methods to prophylactically administer a therapeutic antibody of the invention to individuals who have a known genetic risk of α-synuclein aggregation, e.g., individuals identified as being at risk by analysis of genetic or biochemical markers. Genetic markers of risk toward PD include mutations in the synuclein or Parkin, UCHLI, and CYP2D6 genes, and particularly mutations at position 53 of the synuclein gene. Individuals presently suffering from Parkinson's disease can be recognized from its clinical manifestations including resting tremor, muscular rigidity, bradykinesia and postural instability.

In some specific methods, the subject has concurrent AD and a disease characterized by α-synuclein aggregation (e.g. the presence of Lewy bodies). In some methods, the subject has concurrent Alzheimer's disease and a disease characterized by synuclein accumulation. In some methods, the subject has concurrent AD and PD.

In asymptomatic subjects, treatment can begin at any age. Preferably, treatment begins before or shortly after the time a subject may manifest the synucleinopathy, e.g., when the subject is in her 40 s, 50 s, 60 s, or 70 s. Treatment typically entails multiple dosages of the therapeutic antibody over a period of time. Preferably, the therapeutic antibody is administered in multiple dosages over at least six months.

Treatment can be monitored by assaying antibody, or activated T-cell or B-cell responses to the therapeutic antibody over time. If the response falls, an additional course of therapy may be indicated.

Administration of α-Synuclein Therapeutic Antibodies

The treatment methods of the present invention include administering an amount of one or more therapeutic antibodies of the invention to induce an immunogenic response to α-synuclein in a subject. In prophylactic applications, pharmaceutical compositions or medicaments are administered to a subject at risk of a synucleopathic disease in a dosage regime comprising an amount and frequency of administration of the composition or medicament sufficient to eliminate or reduce the risk, lessen the severity, or delay the outset of the disease, including physiological, biochemical, histologic and/or behavioral symptoms of the disease, its complications and intermediate pathological phenotypes presenting during development of the disease. In therapeutic applications, compositions or medicates are administered to a subject diagnosed with or at risk of such a disease in an administration regime comprising an amount and frequency of administration of the composition sufficient to lessen or completely cure or prevent the physiological, biochemical, histologic and/or behavioral symptoms of the disease, including complications and intermediate pathological phenotypes in development of the disease.

For example, the methods of the invention will result in at least partial clearance of Lewy bodies, at least partial disaggregation of Lewy bodies and/or reduces levels of α-synuclein oligomers in synapses of a treated subject. An amount adequate to accomplish therapeutic or prophylactic treatment is defined as a therapeutically- or prophylactically-effective dose. A combination of amount and dosage frequency adequate to accomplish therapeutic or prophylactic treatment is defined as a therapeutically or prophylactically-effective administration regime. In both prophylactic and therapeutic regimes, therapeutic antibodies of the invention are usually administered in several dosages until a sufficient immune response has been achieved. Typically, the immune response is monitored and repeated dosages are given if the immune response starts to wane.

In some methods, administration of the therapeutic antibody of the invention results in reduction of intracellular levels of aggregated α-synuclein. In some methods, administration of the therapeutic antibody results in improvement in a clinical symptom of a Lewy body disease, such as motor function in the case of Parkinson's disease. In some methods, reduction in intracellular levels of aggregated α-synuclein or improvement in a clinical symptom of disease is monitored at intervals after administration of the therapeutic antibody.

Effective doses of the compositions of the present invention, for the treatment of the above described conditions vary depending upon many different factors, including means of administration, target site, physiological state of the subject, whether the subject is human or an animal, other medications administered, and whether treatment is prophylactic or therapeutic. Usually, the subject is a human but nonhuman mammals including transgenic mammals can also be treated. Treatment dosages need to be titrated to optimize safety and efficacy.

For the therapeutic antibodies of the invention, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg or, in other words, 70 mgs or 700 mgs or within the range of 70-700 mgs, respectively, for a 70 kg subject.

An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to α-synuclein in the subject. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the subject. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

The therapeutic antibodies of the invention can be administered as pharmaceutical compositions comprising a variety of other pharmaceutically acceptable components. See Remington's Pharmaceutical Science (15th ed., Mack Publishing Company, Easton, Pa., 1980). Thus, the therapeutic antibody of the invention can be used in the manufacture of a medicament for treatment of synucleinopathic disease. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. For many indications in which α-synuclein aggregation is targeted in the brain, the therapeutic antibodies of the invention can be administered in conjunction with agents that increase passage of the therapeutic antibodies of the invention across the blood-brain barrier.

The administration route of the therapeutic antibodies of the invention can be administered by any effective means for delivery of the therapeutic antibody to the primary site of the disease. The most typical route of administration is parenteral, although other methods of administration may also be used.

For parenteral administration, the therapeutic antibodies of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/ml, formulated in aqueous buffer consisting of 50 mM L-histidine, 150 mM NaCl, adjusted to pH 6.0 with HCl. Compositions for parenteral administration are typically substantially sterile, substantially isotonic and manufactured under GMP conditions of the FDA or similar body. For example, compositions containing biologics are typically sterilized by filter sterilization. Compositions can be formulated for single dose administration.

In some methods, the therapeutic antibodies of the invention are injected directly into a particular tissue where deposits have accumulated, for example intracranial injection. Intramuscular injection or intravenous infusion are preferred methods for administration of a therapeutic antibody. In specific methods, particular therapeutic antibodies are injected directly into the brain.

EXAMPLES

The following examples are put forth so as to provide those of ordinary skill in the art with a complete disclosure and description of how to make and use the present invention, and are not intended to limit the scope of what the inventors regard as their invention, nor are the examples intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1: Cloning and Sequencing of IGP101 $V_H$ and $V_L$ Regions

Amino acid sequences of the $V_H$ and $V_L$ regions of IGP101 were determined. The amino acid sequences of the $V_H$ and $V_L$ regions of IGP1-1 are depicted below in Table 1. CDRs were determined using the IMGT numbering system to identify the CDR's (Lefranc, M.-P. et al., Dev. Comp. Immunol., 27, 55-77 (2003)).

TABLE 1

IGP101 CDR Sequences

| Antibody | CDR-1 | CDR-2 | CDR-3 | V Region |
|---|---|---|---|---|
| IGP101 $V_L$ | KSLLHSNGNTY (SEQ ID NO: 1) | RMS (SEQ ID NO: 2) | MQHLEFPFT (SEQ ID NO: 3) | DIVMTQAAPSVPVTPGESVS ISCRSSKSLLHSNGNTYLYW FLQRPGQSPQLLIYRMSNLA |

TABLE 1-continued

IGP101 CDR Sequences

| Antibody | CDR-1 | CDR-2 | CDR-3 | V Region |
|---|---|---|---|---|
|  |  |  |  | SGVPDRFSGSGSGTAFTLRI SRVEAEDVGVYYCMQHLEFP FTFGAGTKLELK (SEQ ID NO: 7) |
| IGP101 $V_H$ | GFSFNTYA (SEQ ID NO: 4) | TLSKSNNYAT (SEQ ID NO: 5) | VGAFAY (SEQ ID NO: 6) | EVQLVESGGGLVQPKGTLKL SCAASGFSFNTYAMNWVRQA PGKSLEWVARTLSKSNNYAT YYADSVKDRFTISRDDSQSML SLQMNNLKTEDTAMYYCVGAF AYWGQGTLVTVSA (SEQ ID NO: 8) |

Example 2: IGP101 Binding to α-synuclein Proteins and Peptides

The ability of IGP101 to bind to the α-synuclein full-length protein and peptides was tested. The protein and peptides tested were as follows:
  Full-length human α-synuclein (140 amino acids) (SEQ ID NO:9)
  Peptide 1: α-synuclein amino acids 100-117 (18 amino acids) LGKNEEGAPQEGILEDMP (SEQ ID NO:10)
  Peptide 2: α-synuclein amino acids 108-117 (10 amino acids) PQEGILEDMP (SEQ ID NO:11)

Experiments were performed on a ForteBio Octet Red96 instrument using ForteBio Anti-Mouse IgG (AMC) Biosensors for α-synuclein and Streptavidin Biosensors for the biotinylated peptides in PBS/BSA. The AMC biosensors were loaded with IGP101 at 5 µg/ml, and the sensors quenched with an irrelevant chrompure mouse IgG (Jackson Immunoresearch) for 300 seconds. Baseline recording for 300 seconds was conducted prior to testing binding of full-length α-synuclein protein (SEQ ID NO:9) to IGP101 at multiple concentrations, with α-synuclein association measured for 600 seconds and dissociation for 600 seconds.

The binding of IGP101 to two biotinylated α-synuclein peptides (SEQ ID NO:10 and SEQ ID NO:11) was determined using the Streptavidin biosensors. Biotinylated peptides were loaded at 5 µg/ml for 700 seconds, 300 seconds for baseline recording and then IGP101 association and dissociation measured for 600 seconds each at multiple concentrations. Double reference sensors were employed in all testing to measure and subtract any observed background signal from nonspecific binding or system noise.

Analysis was performed with ForteBio Data Analysis Software (v8.2). After background subtraction, a 1:1 local kinetic model was fit to the observed association and dissociation curves. Overall $K_D$, $K_{on}$, $K_{off}$ and R2 correlation coefficients were determined. Where possible, a global curve fit was also performed for multiple concentrations of the antibody/analyte.

Reference Sensor Background subtraction and 1:1 curve fits gave the following Global $K_D$ values:
  Full-length α-synuclein (SEQ ID NO:9) binding $K_D$—$5.34E^{-9}$
  Peptide 1 (SEQ ID NO:10) binding $K_D$—$1.88E^{-9}$
  Peptide 2 (SEQ ID NO:11) exhibited no detectable binding This binding experiment demonstrates that IGP101 selectively binds to an epitope on α-synuclein that is present in Peptide 1, corresponding to α-synuclein amino acids 100-117 (SEQ ID NO:10), but the IGP101 binding site is not full represented in the shorter peptide, Peptide 2, corresponding to α-synuclein amino acids 108-117 (SEQ ID NO:11), as evidenced by the undetectable binding of IGP101 to Peptide 2 (SEQ ID NO:11).

Example 3: Binding of IGP101 to Secreted Forms of Human α-Synuclein (Prophetic)

The ability of IGP101 to bind to the secreted forms of α-synuclein that are present in cerebral spinal fluid (CSF) is determined.

CSF is obtained from 10 sporadic Parkinson's disease (PD) patients and 10 healthy age-matched subjects (PrecisionMed, Solana Beach, Calif.). 1 ml of CSF from each of the 10 PD patients is pooled and 1 ml of CSF from each of the 10 healthy controls was pooled to obtain enough material to affinity isolate the α-synuclein present in the CSF samples. First, the samples are confirmed to have detectable levels of α-synuclein using a human α-synuclein ELISA kit (ThermoFisher Scientific, Waltham, Mass.). The results confirm that human α-synuclein is detectable in the CSF of both normal controls and PD patients.

The pooled CSF from normal and PD patients is then incubated with IGP101 to determine its ability to bind to the α-synuclein in the CSF, which is presumably secreted α-synuclein. The pooled CSF samples are preincubated with IgG affinity resin followed by synuclein isolation on either 6H7, IGP101 or 8A5 affinity resin for 60 min at room temperature, after which the sample is washed and specifically bound synuclein eluted with 50 mM Glycine, pH 2.3 with 150 mM NaCl into a tube containing 1M TBS, pH 8.3 to neutralize the pH, concentrated on YM10 filters and prepared for synuclein Western blots. Western blots are probed for α-synuclein detection with 12C6 (See, e.g., 20130317199), 2A12 and 8A5 (each at 1 µg/ml), analysis by Odyssey SA software version 1.1.7 (LiCor, Lincoln, Nebr.). 6H7 is an N-terminal synuclein antibody produced from a hybridoma having the ATCC accession number PTA-6910, and 8A5 is a C-terminal synuclein antibody produced from a hybridoma having the ATCC accession number PTA-6909. IGP101 is shown to bind to α-synuclein in the CSF of PD patients and normal patients equal to or better than that seen for antibodies 6H7 and 8A5.

Example 4: Detection of IGP101 Binding to Secreted Synuclein from hiPSC-Derived Dopaminergic Neurons. (Prophetic)

To confirm that the IGP101 is binding to secreted α-synuclein as opposed to α-synuclein present in CSF as a result of lysis, dopaminergic neurons derived from induced pluripotent stem cells (iPSC) of both normal and PD patients are used. Dopaminergic neurons are differentiated in culture from hiPSC according to the methods of US Pat. App No. 20150010514, which is incorporated by reference herein, and as further clarified in Kriks S et al., *Nature.* 2011; 480(7378):547-551; Pruszak J et al., *Stem cells.* 2007; 25(9):2257-2268; and Sundberg M et al., *Stem Cells.* 2013 August; 31(8): 1548-1562. hiPSC-derived neurons cells are stained for surface marker expression profiles after 14 and 30 days of differentiation in vitro as previously described. Pruszak J et al. *Stem cells.* 2009; 27(12):2928-2940.

Antibodies 6H7, 8A5 and IGP101 are used to affinity purify the secreted form of α-synuclein from the supernatant of hiPSC-derived neural cell populations. Dopaminergic neurons are differentiated as described above from hiPSC from both normal and PD patients. The differentiated cells are media conditioned for 3 days, and the media is collected for α-synuclein immunoprecipitation.

Collected conditioned media is centrifuged at 15,000 rpm (4° C.) and supernatants precleared on a mouse IgG (Jackson) Sepharose 4B resin (GE Healthcare) before immunoprecipitation using IGP101, 8A5 or 6H7, each previously coupled to Sepharose 4B resins. After immunoprecipitation, all three bead sets are washed three times with mammalian protein extraction buffer (M-PER, ThermoScientific, Waltham, Mass.) and immunoprecipitated protein extracted from pelleted beads with 2× Laemmli reducing buffer (Sigma, St. Louis, Mo.) and separated on NuPage Bis-Tris protein gels (ThermoScientific, Waltham, Mass.). Western blots are probed for α-synuclein detection with 12C6 (See, e.g., 20130317199), 2A12 and 8A5 (each at 1 µg/ml), analysis by Odyssey SA software version 1.1.7 (LiCor, Lincoln, Nebr.). To ensure the α-synuclein specificity of all 3 immunoprecipitations, the unconditioned growth media is incubated with the 3 antibody conjugated resins in parallel with the conditioned media, and the resultant nonspecific eluate ran as a media control on the Western blot.

IGP101 is shown to bind to α-synuclein in the conditioned media from hiPSC of PD patients and normal patients equal to or better than that seen for antibodies 6H7 and 8A5.

Example 5: Development of an Assay for Confirmation of Synuclein Engagement of IGP101 (Prophetic)

A synuclein ELISA assay is developed to only measure synuclein not bound by IGP101 in mouse ISF and CSF and in primary human dopaminergic neurons in culture conditioned media. This assay is developed to determine how much synuclein is bound to IGP101 and therefore the level of IGP101 target engagement in each study. This assay may also have utility in detection of target engagement by IGP101 in CSF from humans treated with a humanized form of the IGP101 antibody.

The synuclein antibodies used are 12C6 which may compete with IGP101 binding and therefore will not interact with synuclein already bound by IGP101 and MJR1 (Abcam, Cambridge, Mass.), a synuclein antibody that may not compete with IGP101 or with 12C6 binding.

IGP101 treated samples are incubated for 2 hours with 12C6 coated ELISA plates. Plates are washed and streptavidin-conjugated 1H7 is added for 60 minutes, plates washed and then the plate is read on Envision plate reader (Perkin Elmer). Synuclein levels are interpolated from an 8 point synuclein protein standard curve and analyzed using linear curve fit in Excel.

The total-synuclein ELISA uses the anti-α-synuclein antibody Ab190376 (Abcam, Cambridge, Mass.) for capture and biotinylated anti-α-synuclein antibody, MJR1 (Abcam, Cambridge, Mass.), for detection, neither or which should compete with IGP101 for binding to synuclein. The Ab190376 antibody diluted in PBS is coated on high binding ELISA plates (Costar—Corning) at 1 µg/ml overnight at 4° C. and plates blocked with 1% Casein (VectorLabs)/PBS for 2 hours at room temperature. Samples are diluted in 0.1% Casein/PBS and incubated for 2 hours at 4° C. Plates are washed and total synuclein levels detected with 1 hour incubation with biotinylated synuclein antibody MJR1, followed by addition of Streptavidin-HRP (Southern Biotech) and then 3,3',5,5'-tetramethylbenzidine substrate (TMB) (ThermoScientific, Waltham, Mass.), assay was stopped with 1 M sulfuric acid (Sigma), and the absorbance read on a Beckman plate reader at 450 nm. Synuclein levels were interpolated from an 8 point synuclein protein standard curve diluted in 0.1% Caesin/PBS and analyzed using 4-Parameter Sigmoidal Curve Fit (GraphPad Prism).

Example 6: Detection of Human α-Synuclein in Human Brain Homogenates (Prophetic)

Samples of normal human brains and brains from patients diagnosed post-mortem with PD are obtained from Banner Health (Sun City, Ariz.). Differential extraction is performed for the normal and PD affected brains after homogenizing the brain regions containing the substantia nigra with a potter-type mechanical homogenizer (VOS 14 S40, rate: 750 rpm; VWR) in 10:1 weight-volumes of ice-cold Tris-proteinase-phosphatase-inhibitor buffer (TPPI-buffer) containing 20 mM Tris-HCl (pH 7.4), 150 mM NaCl, 1 mM ethylene diamine tetraacetic acid (EDTA, Merck), 1 mM ethylene glycol tetraacetic acid (EGTA, Sigma-Aldrich), 5 mM sodium pyrophosphate (Sigma), 30 mM sodium fluoride (Sigma-Aldrich), 1 mM PMSF (Sigma), 2 mM sodium vanadate, 10 mM 1,10-phenanthroline monohydrate (Sigma-Aldrich), 5 µg/ml soybean trypsin inhibitor, 5 µg/ml pepstatin and a cocktail of proteinase inhibitor (CPI, Roche Diagnostics GmbH, Germany) Half of the total homogenate (TotH) is stored at −80° C. and the remainder centrifuged (136000×g, 60 mM at 4° C.; TLA-55 rotor, OptimaTMTLX Ultracentrifuge, Beckman Coulter) to generate a Tris-soluble fraction (SF).

The supernatant is separated from the pellet, aliquoted and stored at −80° C. The pellet is solubilized in nine volumes high salt (0.85 M NaCl) containing TPPI-buffer and centrifuged (20000×g, 30 min, 4° C.). The resulting high-salt pellet is stored at −80° C. The second supernatant is brought to a concentration of 1% Sarkosyl by adding 10% Sarkosyl, and the 1% Sarkosyl supernatant is incubated at room temperature for 60 min in a top-over-top rotary tumbler and then centrifuged (136000×g, 60 min, 4° C.). The third Sarkosyl soluble supernatant is stored at −80° C. and the Sarkosyl-insoluble pellet is resuspended in 30 µl TPPI buffer and aliquoted.

For application of conventional SDS-PAGE and Western blotting, samples obtained are diluted in 1× sample buffer for SF and IF and 2× sample buffer for TotH (final concentrations 1× sample buffer: 1% (w/v) SDS and 2.5% (v/v) 2-mercaptoethanol) based on fresh weight concentration. The samples are denatured and reduced by heating at 95° C. for 10 min and separated on 7.5% Tris-HCl gels (Criterion XT Precast Gel, 26-well comb, 10 µl, 1.0 mm; Biorad). Proteins are dry electrotransferred (iBlot™, Invitrogen) to PVDF-membranes (iBlot™ Gel Transfer Stacks, PVDF, Regular, Invitrogen). Membranes are first washed in 0.4% PFA for 30 min and then in Tris-buffered saline. Next the membranes are incubated in Tris-buffered saline (TBS, pH 7.6) containing 5% (w/v) non-fat dry milk and 0.1% (v/v) Tween-20 for 1 hour.

Blots are incubated with IGP101, 8A5 or 6H7 overnight at concentrations of 1 µg/ml. After washing and incubation with an anti-mouse HRP-conjugated secondary antibody (goat-anti-mouse or IgG, DAKO) blots are developed using the ECL detection system (SuperSignal West Femto Maximum Sensitivity Substrate, product 34096, Thermo Scientific) and images recorded digitally (VisionWorks Acquisition, UVP) with different exposure times. Dedicated software (VisionWorks Analysis, UVP) is used for analysis of the blots. Samples of three TotH and the Sarkosyl soluble fractions of each gel are run as an inter-gel reference gel. Loading of the Sarkosyl insoluble fractions on different gels is standardized using three identical reference samples loaded on every gel.

The studies show that IGP101 binds to the α-synuclein found in the homogenized brain tissue of PD patients.

Example 7: Detection of Human α-Synuclein in Free-Floating Vibratome Sections (Prophetic)

In situ detection of α-synuclein is also detected in human brain slices containing the substantia nigra from normal human brains and brains from patients affected with PD. From each of the human brain samples, brain regions that include the substantia nigra and six control sections are selected based on guidance from *Atlas of the Human Brain*, Fourth Edition (by Mai J K and Majtanik, M, Eslevier, Dec. 14, 2015). The six sections containing the substantia nigra and six control sections are each stained for 6H7, IGP101 and 8A5. Briefly, the free-floating sections are incubated in Corning Netwells™ (Sigma Aldrich, St. Louis, Mo.) in two batches, one for staining and one for counterstaining. Sections are washed twice in PBS and incubated for 20 minutes in hydrogen peroxide 1.5% in PBS and methanol (1:1) to remove endogenous peroxidase activity. After washing the sections three times in PBS containing 0.1% Triton X100 (PBST), the sections are blocked for 60 min in 10% Fetal Calf Serum (FCS) in PBST followed by an overnight incubation with primary antibodies 6H7, IGP101 and 8A5 in PBST with 10% FCS. After rinsing, the sections are incubated with goat anti mouse peroxidase labeled (GAMPO) secondary antibody (DAKO, 1/500 in PBST, 10% FCS) and the signal is developed with 3,3' diaminobenzidine tetrahydrochloride (DAB, 1 tablet per 10 ml Tris-HCl with 3 µl $H_2O_2$ per 10 ml). Sections are counterstained with Mayer's hematoxylin, dehydrated in five steps (50, 70, 95 and 2×100%) in ethanol and xylene (Merck Eurolab) and mounted in Depex (Depex mounting medium, BDH Laboratory).

The studies show that IGP101 binds to the α-synuclein found in the substantia nigra of PD patients.

Example 8: Disruption of Synuclein Aggregation by IGP101 in an Ex Vivo Model (Prophetic)

The ability of IGP101 to disrupt synuclein aggregation is tested in a neuronal cell-based model of synuclein aggregation as described in US Pat App 20130337463. Briefly, in this model, small seeds of pre-formed α-synuclein or secreted α-synuclein fibrils generated from recombinant α-synuclein or secreted α-synuclein are added directly to primary neurons. Small amounts of these pre-formed α-synuclein fibrils are endocytosed by the neuron, without the addition of other factors to assist entry into the neuron. These seeds of pre-formed α-synuclein fibrils induce recruitment of endogenously expressed α-synuclein into abnormal, phosphorylated, insoluble, ubiquitinated aggregates. Formation of these aggregates from endogenous α-synuclein in primary neurons derived from wild type, non-transgenic mice follows an initial lag phase of 2-4 days. By 4-7 days small, punctate insoluble, phosphorylated aggregates from in presynaptic terminals and axons. By 7-10 days post-pre-formed α-synuclein fibril addition, the aggregates grow and become more elongated and serpentine in appearance, resembling Lewy Neurites. They also can be found in approximately 30% of neuronal soma and dendrites where they appear skein-like, but over time form condensed accumulations that resemble Lewy Bodies. Neuron death is negligible prior to 14 days after adding the pre-formed α-synuclein fibrils. This permits the careful examination of α-synuclein aggregates from their initial early formation, to spread throughout the neuron, and ultimately neuron death, as well as how neuronal function may be perturbed at each of these stages.

A critical aspect of this model is that aggregation does not occur when pre-formed α-synuclein fibrils are added to primary neurons from α-synuclein knockout mice. For example, the pre-formed α-synuclein fibrils themselves are not phosphorylated, and therefore when they are added to α-synuclein knockout neurons, there is no p-α-synuclein visible by immunofluorescence or immunoblot. Furthermore, addition of fibrils to neurons from α-synuclein knockout mice does not cause cell death, or changes in neuronal synchronous firing, excitation or connectivity. Thus, the pathological phenotypes are caused by "seeded" corruption of endogenous α-synuclein likely through both a loss of normal α-synuclein function and gains of toxic functions from the accumulation of the Lewy Neurite and Lewy Body-like inclusions, rather than exposure to the synthetic fibrils themselves.

Pre-formed synuclein or secreted α-synuclein fibrils are prepared to seed primary neurons from normal mice. Purified α-synuclein and secreted α-synuclein monomer is thawed and centrifuged at 100,000×g at 4° C. for 60 minutes to pellet any aggregated material. The supernatants are removed, and diluted in PBS into a sterile 1.5 ml microcentrifuge tube to final volume of 500 µl and final concentration of 5 mg/ml. The tube is shaken for 7 days at 1000 RPM to create the fibrils.

Neurons are cultured using dissected hippocampus tissue from normal and α-synuclein knock out mice. Cultures from α-synuclein knockout mice can be used as a control to confirm that phenotypes result from aggregates formed from endogenously expressed α-synuclein and not from addition of pre-formed α-synuclein and secreted α-synuclein fibrils. The dissected tissue is placed in 15 ml Falcon tube with 10 ml of Hibernate E (Gibco, ThermoFisher, Waltham, Mass.) on ice. The tissue is rinsed 2× with HBSS and filter sterilized using a papain solution and a 0.20 µm syringe filter (Fisher Scientific, SLLG025SS). Additional papain solution is added to a total volume of 10 ml, and the tissue incubated for 30-60 min 50 µL DNase solution to 10 ml buffer and added to tissue. The tissue is rinsed once in buffer and 2× with HBSS. The final HBSS rinsed is removed so that around 1 ml of total volume remains.

The neurons are counted and plated in a 24 well plate (approx. 100,000 cells/well), a 6 well plate ($0.5 \times 10^6$ cells/well) and a 6 cm vessel ($1 \times 10^6$ cells/well). When neurons are 5-10 days in vitro (DIV 5-10) the pre-formed fibrils are added. Approximately 80% of media from the well of the neurons is removed, and the pre-formed fibril solution created as described above is added to sterile PBS to final concentration of 0.1 mg/ml. The mixture is sonicated with 60 pulses at 10% power (total of 30 sec, 0.5 sec on, 0.5 sec off). The sonicated pre-formed fibrils are diluted and used alone or with antibody 6H7, IGP101 or 8A5 added to the tissue to a final concentration of 1 μg/ml. The neurons are incubated for a further 7-23 days, with ~50% of media changed once a week. The media of the samples with 6H7, IGP101 or 8A5 antibody contains levels of antibody to retain a consistent level of antibody throughout the incubation period.

The pre-formed fibril transduction and seeding can be confirmed by immunofluorescence or sequential extraction and immunoblotting. Abnormal α-synuclein derived from endogenous α-synuclein can be detected via immunofluorescence with a p-α-synuclein specific antibody. These phosphorylated inclusions are not visible when pre-formed fibrils are added to α-synuclein knockout neurons or added in combination with IGP101. Alternatively, the neurons can be fixed with 4% paraformaldehyde/4% sucrose/1% Tx-100 and stained with an antibody to total α-synuclein. The normal, "synaptic" α-synuclein is not visible, but the pre-formed fibrils-induced α-synuclein inclusions are not extracted and are visible by immunofluorescence.

To distinguish exogenously added human pre-formed fibrils from inclusions formed from endogenous α-synuclein, neurons can be co-stained using an antibody that is specific for human α-synuclein (e.g., LB509 or Syn204, ThermoFisher Scientific, Waltham, Mass.) and an antibody for p-α-synuclein (e.g., MJFR1, Abcam, Cambridge, Mass.).

The neurons from normal mouse displayed synuclein aggregation upon seeding with the preformed fibrils from α-synuclein or from secreted α-synuclein, whereas the neurons from synuclein knockout mice and the neurons treated with both pre-formed fibrils and IGP101 antibodies showed a reduction in the synuclein aggregation as compared to the normal cells receiving only the preformed fibrils.

Example 9: IGP101 Antibody Reduce the Level of α-Synuclein Aggregation and Symptoms of Parkinson's Disease in an In Vivo Model (Prophetic)

The effect of the IGP101 antibody is tested using an in vivo model of Parkinson's disease, an α-synuclein transgenic mouse model expressing the human α-synuclein cDNA under the murine Thy-1 promoter (The PsychoGenics Line 61 mice; see Rockenstein, E. et al. *Journal of neuroscience research* 68, 568-578 (2002)) (PsychoGenics, Tarrytown, N.Y.). The Line 61 mice present many of the characteristics of human Parkinson's disease, including lack of coordination at 4 months, cognition deficit at 4.5 months, increased total activity in open field by 7 months, hypolocomotion by 14 months and presence of α-synuclein positive aggregates histopathologically. Accumulation of phosphorylated Serine 129 residues in the striatum and substantia nigra that might modulate the formation of protein aggregation like inclusion bodies and fibrils is evident by 9 months of age in this model (Chesselet, M. F. et al. *American Society for Experimental NeuroTherapeutics* 9, 297-314 (2012)). IGP101 is tested in the Line 61 mice for its effects on coordination, cognition, total activity in open field and presence of α-synuclein and pSer129-α-synuclein positive aggregates histopathologically.

Line 61 mice (3 months old; n=40) are treated with either a control IgG or IGP101. IgG control and IGP101 antibodies are injected intraperitoneally at a concentration of 10 mg/kg for 24 weeks. During the 24 week administration after the beginning of the antibody treatment regimen, the mice are tested for coordination, cognition deficit and increased total activity in open field. Impaired motor coordination in the treated mice is measured by increased foot slips in the tapered beam and overall gait measures and paw positioning in the NeuroCube® system (PsychoGenics, Tarrytown, N.Y.). Cognition and locomotor activity is assessed using the Open Field Test and PhenoCube® (PsychoGenics, Tarrytown, N.Y.). The Line 61 mice treated with IGP101 display a statistically significant increase in overall concentration.

The treated mice are also sacrificed at nine months old and assessed histopathologically to determine both the presence and levels of α-synuclein positive aggregates histopathologically. Accumulation of phosphorylated Serine 129 residues in the striatum and substantia nigra which might modulate the formation of protein aggregation like inclusion bodies and fibrils is also assessed at this time in these mice. The mice treated with IGP101 display a statistically significant decreased level of both α-synuclein positive aggregates and phosphorylated Serine 129 compared to their control counterpart mice receiving only IgG.

Example 10: Humanized α-Synuclein Antibodies of the Invention (Prophetic)

Humanized variants of IGP101 are generated that comprise CDR sequences derived from mouse monoclonal antibody IGP101. The cell line producing the antibody IGP101 has the ATCC accession number PTA-9197, and was deposited under the provisions of the Budapest Treaty with the American Type Culture Collection (ATCC, Manassas, Va. 20108) on May 8, 2008.

The heavy chain variable $V_H$ region of IGP101 is cloned by RT-PCR using mRNA prepared from hybridoma cells. Consensus primers are employed to $V_H$ region leader peptide encompassing the translation initiation codon as the 5' primer and a g2b constant regions specific 3' primer. Exemplary primers are described in U.S. patent publication 2005/0009150. The sequences from multiple, independently-derived clones, can be compared to ensure no changes are introduced during amplification. The light chain variable $V_L$ region of IGP101 is cloned in an analogous manner as the $V_H$ region using a consensus primer set designed for amplification of murine $V_L$ regions. These primers are designed to hybridize to the $V_L$ region encompassing the translation initiation codon, and a 3' primer specific for the murine Ck region downstream of the V-J joining region. Exemplary primers are described in US2005/0009150. The cloned sequences are then combined with sequences encoding human constant regions.

The heavy and light chain variable regions are engineered to encode splice donor sequences downstream of the respective VDJ or VJ junctions, and cloned into the mammalian expression vector, such as pCMV-hγ1 for the heavy chain, and pCMV-hκ1 for the light chain. These vectors encode humanγ1 and Ck constant regions as exonic fragments downstream of the inserted variable region cassette. Following sequence verification, the heavy chain and light chain expression vectors can be co-transfected into COS cells to produce chimeric antibodies. Conditioned media is collected 48 hours post transfection and assayed by western blot analysis for antibody production or ELISA for antigen binding.

Example 11: Testing the Immunogenicity of Humanized IGP101 Antibodies (Prophetic)

An EpiScreen™ assay (Antitope, Cambridge, UK) is used to assess the humanized anti-α-synuclein antibodies of Example 10 for immunogenic potential. See, e.g., Jones et al. (2004) J. Interferon Cytokine Res. 24:560; and Jones et al. (2005) J. Thromb. Haemost. 3:991. Time course T cell assays are performed using $CD8^+$-depleted peripheral blood mononuclear cells (PBMC); and T cell proliferation was measured by incorporation of $^{3H}$-thymidine at various time points after addition of test antibody samples.

PBMC were isolated from healthy normal donor buffy coats created from blood drawn within 24 hours of testing. T cell responses to the humanized IGP101 antibodies are compared to a clinical standard antibody. The humanized IGP101 antibodies are added to PBMC cultures in vitro to a final concentration of 50 μg/ml in culture medium. A clinical antibody control and a culture medium-only control are included as positive and negative control samples, respectively. The control and test samples are incubated for 8 days at 37° C. with 5% $CO_2$. On days 5, 6, 7, and 7, the cells in the test and control samples are suspended and transferred to wells of a multi-well culture plate. The test and control samples are pulsed with 0.75 μCi $[^{3H}]$-thymidine and incubated for a further 18 hours before collecting onto filter mats. Counts per minute (cpm) for each well are determined using scintillation counting.

For proliferation assays, a threshold of a stimulation Index ("SI") equal to or greater than 2 are used, where samples inducing a proliferative response above this threshold are considered positive. The SI used is the mean test sample counts divided by the mean of the unstimulated control. The humanized IGP101 antibodies that display a low immunogenic potential (with an SI of less than 2) are considered clinical candidates for further development as therapeutic antibodies for human clinical treatment.

Example 11: Pharmacokinetics of IGP101 in Mice

The half-life of various anti-α-synuclein antibodies, including IGP101, were tested in mice to determine the pharmacokinetic profile and potential dosing needed for efficacy. C57/Bl6 female mice (n=6) were provided a single intravenous dose of 10 mg/kg of the antibodies as listed in FIG. 1, and blood was drawn from drawn at 30 minutes, 4 hours, 1, 3, 7, 10 and 14 days (staggered collections for n=3/time point). Administered antibody levels in plasma were detected by binding to synuclein coated ELISA plates and anti-mouse antibody detection.

As shown in FIG. 1, the tested anti-α-synuclein antibodies, with the exception of 2A12, have half-lives as expected in mice. Based on the pharmacokinetic profile of the antibodies, shown in line graph form in FIG. 2, once per week dosing of IGP101 is sufficient for efficacy.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. All references cited herein are incorporated by their entirety for all purposes. In the claims that follow, unless the term "means" is used, none of the features or elements recited therein should be construed as means-plus-function limitations pursuant to 35 U.S.C. § 112, 16.

The invention claimed is:

1. A therapeutic monoclonal antibody comprising the VL CDRs of SEQ ID NO:1, SEQ NO:2 and SEQ NO: 3 and comprising the VH CDRs of SEQ ID NO:4, SEQ NO:5 and SEQ NO: 6.

2. The therapeutic antibody of claim 1, wherein the antibody comprises a VH region having substantial identity to SEQ NO:8.

3. The therapeutic antibody of claim 1, wherein the antibody is a humanized monoclonal antibody.

4. The therapeutic antibody of claim 3, wherein the humanized antibody comprises a heavy chain region of the isotype IgG1, IgG2, IgG3, or IgG4.

5. The therapeutic antibody of claim 3, wherein the humanized antibody is an Fv, scFv, Fab, F(ab')2, or Fab'.

6. A method of treating a disease characterized by a-synuclein aggregation comprising administering to a subject having or at risk of the disease a therapeutic antibody comprising an antibody of claim 1.

7. The method of claim 6, wherein the method comprises administering to a subject having or at risk of the disease a therapeutic antibody comprising an antibody of claim 1.

8. The method of claim 6, wherein the disease is Parkinson's disease, Parkinson's disease with Alzheimer's disease, multiple system atrophy, or dementia with Lewy bodies.

9. The method of claim 6, wherein the antibody is administered at a dosage of 0.0001 to 100 mg antibody/kg body weight.

10. The method of claim 6, wherein the therapeutic antibody is administered with a pharmaceutical carrier.

11. The method of claim 6, wherein the therapeutic antibody is administered in multiple dosages over at least six months.

12. The method of claim 6, wherein the disease is Parkinson's disease.

* * * * *